(12) United States Patent
Itozaki (10) Patent No.: US 8,525,515 B2
(45) Date of Patent: Sep. 3, 2013

(54) EQUIPMENT FOR INSPECTING EXPLOSIVES AND/OR ILLICIT DRUGS, ANTENNA COIL AND METHOD FOR INSPECTING EXPLOSIVES AND/OR ILLICIT DRUGS

(75) Inventor: Hideo Itozaki, Suita (JP)

(73) Assignee: Osaka University, Suita-shi, Osaka (JP)

( * ) Notice: Subject to any disclaimer, the term of this patent is extended or adjusted under 35 U.S.C. 154(b) by 304 days.

(21) Appl. No.: 13/122,466

(22) PCT Filed: Oct. 2, 2009

(86) PCT No.: PCT/JP2009/067262
§ 371 (c)(1),
(2), (4) Date: Apr. 4, 2011

(87) PCT Pub. No.: WO2010/041607
PCT Pub. Date: Apr. 15, 2010

(65) Prior Publication Data
US 2011/0181281 A1    Jul. 28, 2011

(30) Foreign Application Priority Data
Oct. 6, 2008    (JP) .................................. 2008-259785

(51) Int. Cl.
*G01V 3/00*    (2006.01)

(52) U.S. Cl.
USPC ......................................... 324/300; 324/322

(58) Field of Classification Search
USPC ........................... 324/300–322; 600/407–445
See application file for complete search history.

(56) References Cited

U.S. PATENT DOCUMENTS

| 4,839,594 A | 6/1989 | Misic et al. |
| 5,206,592 A | 4/1993 | Buess et al. |
| 5,365,171 A | 11/1994 | Buess et al. |

(Continued)

FOREIGN PATENT DOCUMENTS

| JP | 1-160539 A | 6/1989 |
| JP | 5-223758 A | 8/1993 |

(Continued)

OTHER PUBLICATIONS

Harpen, "The Theory of Shielded Loop Resonators," Magnetic Resonance in Medicine, vol. 32, 1994, pp. 785-788.

(Continued)

*Primary Examiner* — Brij Shrivastav
(74) *Attorney, Agent, or Firm* — Birch, Stewart, Kolasch & Birch, LLP.

(57) ABSTRACT

Equipment for inspecting explosives and/or illicit drugs comprises a means for generating high-frequency pulses, an antenna coil which irradiates an object of inspection with the generated high-frequency pulses working as a radio wave and receives a nuclear quadrupole signal which is generated from the object of inspection when the object of inspection is excited by the radio wave, and a means for detecting explosives and/or illicit drugs in the object of inspection based on the nuclear quadrupole signal thus received, wherein the antenna coil is formed in the shape of a figure of "8" by using a high-frequency coaxial cable so that two solenoid coil portions wound reversely to each other can be provided, and is used while facing the object of inspection. Various explosives and/or illicit drugs can be inspected compactly and surely by the equipment for inspecting explosives and/or illicit drugs and an inspecting method using such equipment for inspecting explosives and/or illicit drugs.

4 Claims, 6 Drawing Sheets

(56) References Cited

U.S. PATENT DOCUMENTS

| | | | |
|---|---|---|---|
| 6,054,856 A * | 4/2000 | Garroway et al. | 324/318 |
| 7,327,137 B1 * | 2/2008 | Crowley et al. | 324/300 |
| 7,511,500 B2 * | 3/2009 | Schiano et al. | 324/318 |
| 7,595,638 B2 * | 9/2009 | Crowley | 324/300 |
| 7,671,586 B2 * | 3/2010 | Crowley et al. | 324/300 |
| 8,278,921 B2 * | 10/2012 | Crowley | 324/300 |
| 2006/0113998 A1 | 6/2006 | Itozaki et al. | |
| 2006/0122484 A1 | 6/2006 | Itozaki et al. | |

FOREIGN PATENT DOCUMENTS

| | | |
|---|---|---|
| JP | 7-502110 A | 3/1995 |
| JP | 2003-24294 A | 1/2003 |
| JP | 2003-512592 A | 4/2003 |
| JP | 2004-177130 A | 6/2004 |
| JP | 2004-177131 A | 6/2004 |
| JP | 3542598 B2 | 7/2004 |
| JP | 2005-55218 A | 3/2005 |

OTHER PUBLICATIONS

Itozaki, "Kenkyu Shuryo Houkokusho," Aug. 21, 2008, pp. Itozaki T-1 to Itozaki T-33.

Konnai et al., "8th National Maritime Research Institute R & D Presentation Conference," Jun. 18, 2008, pp. 279-280.

Stensgaard, "Optimized Design of the Shielded-Loop Resonator," Journal of Magnetic Resonance, Series A, vol. 122, Article No. 0187, 1996, pp. 120-125.

Stensgaard, "Planar Quadrature Coil Design Using Shielded-Loop Resonators," Journal of Magnetic Resonance, vol. 125, Article No. MN961103, 1997, pp. 84-91.

Stievater et al., "A Trimodal Resonator for Three Mutually Perpendicular Magnetic Fields," Review of Scientific Instruments, vol. 70, No. 3, Mar. 1999, pp. 1780-1786.

Suits et al., "14N Magnetic Resonance for Materials Detection in the Field," Solid State Nuclear Magnetic Resonance, vol. 24, 2003, pp. 123-136.

Suits et al., "Noise-Immune Coil for Unshielded Magnetic Resonance Measurements," Journal of Magnetic Resonance, vol. 131, Article No. MN971335, 1998, pp. 154-158.

Suits et al., "Surface and Gradiometer Coils near a Conducting Body: The Lift-off Effect," Journal of Magnetic Resonance, vol. 135, Article No. MN981608, 1998, pp. 373-379.

Translation of International Preliminary Report on Patentability dated May 19, 2011 for International Application No. PCT/JP2009/067262 (Forms PCT/IB/338 and PCT/IPEA/409).

International Search Report, PCT/JP2009/067262, Dec. 28, 2009.

* cited by examiner

EQUIPMENT FOR INSPECTING EXPLOSIVES AND/OR ILLICIT DRUGS, ANTENNA COIL AND METHOD FOR INSPECTING EXPLOSIVES AND/OR ILLICIT DRUGS

TECHNICAL FIELD

The present invention relates to a device for detecting explosives and illicit drugs, an antennal coil, and a method for detecting explosives and illicit drugs. In particular, it relates to an explosive/illicit drug detection device suitable to reliably detect explosives and illicit drugs hidden in luggage loaded in aircrafts etc., an antenna coil used in the detection device, and an explosive/illicit drug detection method using the detection device.

BACKGROUND ART

In light of terrorist bomb explosion incidents, illicit drug smuggling incidents, and so on, that have happened frequently in recent years, inspections of suspicious substances are conducted by using metal detection devices and X-ray inspection devices, and so on at traffic terminals such as airports, public facilities, and so on. However, it is difficult to detect explosives and illicit drugs put in plastic containers. Thus inspectors depend on drug sniffing dogs and so on under present circumstances; therefore it is difficult to say that security measures are sufficiently taken.

In view of such circumstances, use of a detection devices using nuclear quadrupole resonance (hereinafter referred to as "NQR detection device") has been proposed in recent years (see Patent Document 1, for example).

In NQR detection devices, the inspection object is irradiated with a high-frequency pulse from a transmitting coil as a radio wave having a frequency specific to the inspection object, i.e., a resonance frequency, the nuclear quadrupoles of the inspection object are excited by the radio wave, a receiving coil receives a nuclear quadrupole signal (hereinafter also referred to as "NQR signal") induced after the irradiation of the radio wave, the receiving coil amplifies the NQR signal, and a substance(s) included in the inspection object is detected, analyzed, and identified. As a result, an explosive, an illicit drug, or the like put in a plastic container can be detected.

In conventional NQR detection devices, however, inspection has been done with an inspection object placed within the transmitting/receiving solenoidal coil of each detection device.

Frequency of the radio wave for irradiation is about 500 kHz to 4 MHz, and external noises are high in level at such a radio frequency range. As a result, the external noises sometimes affect the inspection signal. Due to this reason, there was a need to take measures against the noises at the time of inspection. In conventional NQR detection devices, there was a need to provide a electromagnetic shield outside the transmitting/receiving coil to completely suppress environmental noises.

Figure 9:
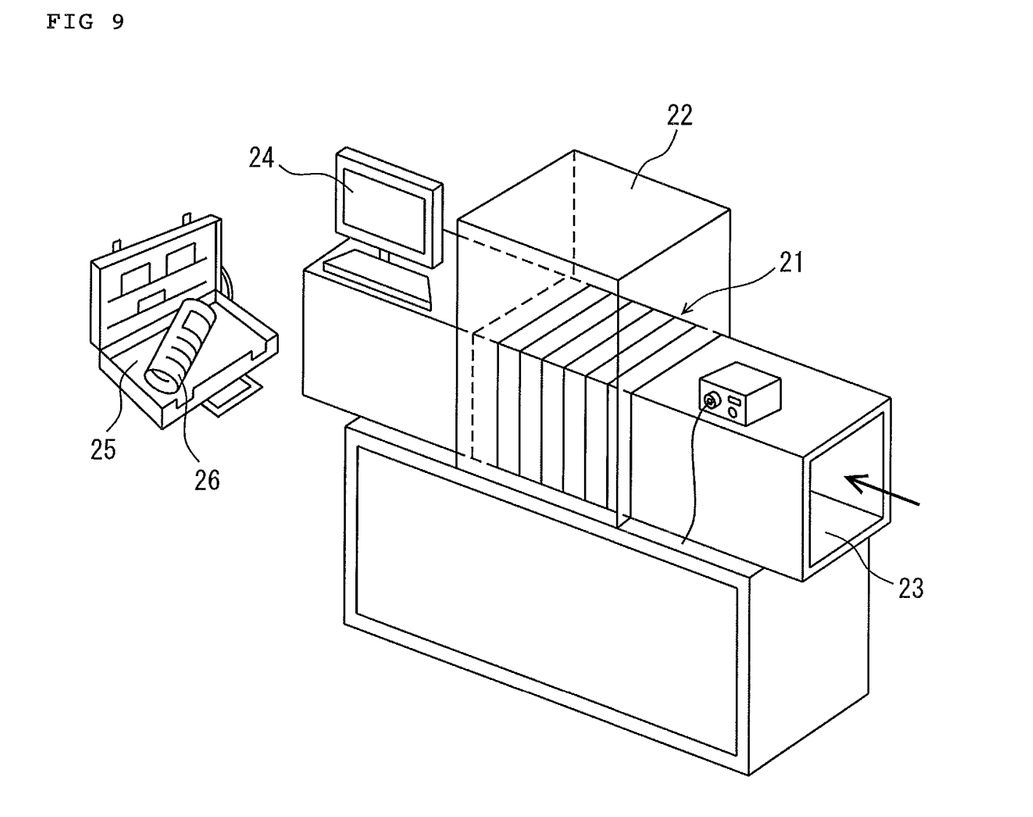
FIG. 9 is an illustration schematically showing a structure of a conventional hand luggage inspection device using nuclear quadrupole resonance.

FIG. 9 shows a hand luggage inspection detection as an example of conventional NQR detection devices. In FIG. 9, reference numeral 21 denotes an antenna coil. Reference numerals 22 and 23 each denote an electromagnetic shield having a tunnel structure, and the antenna coil 21 is completely covered with the electromagnetic shield 22 and 23. And further, at a bottom portion of the electromagnetic shield 23, a belt conveyor (not shown) is provided. Reference numeral 24 denotes a personal computer (PC). The above components are placed on an installation stage in which an electronic circuit is housed.

A bag 25, in which an inspection object 26 is put, is conveyed into the tunnel-type electromagnetic shield 23, and passes through the antenna coil 21 shielded from external noises by the electromagnetic shields 22 and 23. At that time, the antenna coil 21 irradiates the bag 25 which the inspection object 26 is put in with a radio wave having a predetermined wavelength, following which a NQR signal is received. The received NQR signal is processed by the PC 24. When an explosive or an illicit drug has been detected as a result of the processing, an image of the substance is displayed on the screen of the PC 24. And further, a warning lamp (not shown) may light up as necessary.

PRIOR ART DOCUMENT

Patent Document

[Patent Document 1] JP-A-5-223758

SUMMARY OF THE INVENTION

Problems to be Solved by the Invention

In conventional NQR detection devices, inspection is conducted with an inspection object placed within the transmitting/receiving solenoidal coil of the device as described above. Thus the antenna coil and the electromagnetic shields are large; therefore, those detection devices were large for detection devices. Moreover, inspection objects have become large in recent years, and thus the use of a larger inspection device has been required. And furthermore, there has been an increasing demand to conduct body checks and shoe inspections. Because of these, it has been desired that a NQR detection device be developed that is compact in size and is capable of reliably detecting various explosives and illicit drugs.

Means of Solving the Problems

The present inventors conducted extensive studies in order to solve the above problems. As a result, it was found that the above problems can be solved by employing following means, and thus the present invention has been accomplished.

The invention is an explosive/illicit drug detection device comprising
a mean for generating a high-frequency pulse;
an antenna coil that irradiates an inspection object with the generated high-frequency pulse as a radio wave and receives a nuclear quadrupole signal sent out of the inspection object excited by the radio wave; and
a detection mean for detecting an explosive and/or an illicit drug hidden in the inspection object based on the received nuclear quadrupole signal,
wherein the antenna coil is formed by winding a high-frequency coaxial cable in the form of a FIG. 8 so that two solenoidal coil portions are provided with the coil portions wound in mutually opposite directions and is used so that it is opposed to inspection objects.

The present inventors considered that a detection device can be made compact by making it possible to inspect an inspection object without placing the inspection object within a transmitting/receiving coil of the device and by considerably reducing noise incurred at the antenna coil through by using a simple technique, and then conducted extensive studies to develop a concrete method.

As a result, it was found that noise can be considerably reduced without providing an electromagnetic shield covering an antenna coil, as found in conventional detection devices, by using a method in which an antenna coil is made by using a high-frequency coaxial cable in the form of a FIG. 8 such that two solenoidal coil portions are provided with the coil portions wound in mutually opposite directions and in which the antenna coil is used as it is opposed to an inspection object. That is, since the high-frequency coaxial cable is a cable made by covering a conductor wire with an electromagnetic shielding material, nearby electric field noises can be reduced by using the high-frequency coaxial cable and also magnetic field noises from distant places can be reduced by forming the two solenoidal coil portions, wound in mutually opposite directions, in the form of a FIG. 8.

Since the noises incurred at the antenna coil can be considerably reduced by the above-mentioned method, a sufficiently high detection sensitivity can be achieved even when the size of the antenna coil is minimized. Following upon the achievement, individual components constituting the inspection device other than the antenna coil can be made compact, and, as the result, the entire inspection device can be made compact.

The making of such a small antenna coil makes it possible to achieve a shift from conventional limited application areas, such as hand luggage inspection devices, to various application areas. For example, in the case where a hand-held body checker has been fabricated by separating an antenna coil from a main body of a detection device and then connecting the antenna coil to the main body by a cable, explosives and illicit drugs hidden in clothes and bodies can be detected by merely bringing the small and light antenna coil close to the clothes and the bodies.

Such a hand-held detection device can also be used as a luggage inspection device used at airports, customhouses, and so forth. Therefore, at the time of inspections of imported goods and so on, explosives and illicit drugs hidden in the substances other than metal that does not allow radio waves to pass through them, such as wood, earthenware, and plastic, can be detected by merely bringing the small and light antenna coil close to the inspection objects.

In the USA etc., it is mandatory at present to conduct X-ray inspections with shoes taken off at the time of explosive detection. The fact is that it is difficult to detect explosives and so on even when X-ray inspections are conducted with shoes taken off. However, in the case where the detection device according to the present invention is used, explosives and so on can be reliably detected by merely getting on the device with shoes on. That is, inspections can be conducted very simply and easily.

A shape and a diameter of the solenoidal coil portions of the antenna coil according to the invention are suitably determined according to used of individual detection devices. For example, with a detection device for body checking and a detection device for mine detection, their coil portions are shaped into a circle and the diameters of the coil portions are set to about 15 cm and about 26 cm, respectively. And further, with a shoe inspection device, solenoidal coil portions are shaped into a hollow ellipse based on shapes of soles of shoes. Moreover, when the winding number of the coil of each solenoidal coil portion is too large, an inductance and a capacity of the cable become too high, and thus it is difficult to tune is to a frequency of a transmitted/received NQR signal. Therefore, the solenoidal coil portions with a winding number of about 2 are preferably used.

The invention is further an explosion/illicit drug detection device, wherein a recessed portion is provided at a part of shielded portion of the high-frequency coaxial cable.

By providing the recessed portion at the shielded portion of the high-frequency coaxial cable, magnetic flux can be made to pass through the cable readily, whereby the detection sensitivity can be further improved.

It is preferable that the recessed portion be provided at one place in central part of the antenna coil. In the high-frequency coaxial cable, when its diameter is too small, shielding properties and pressure-resisting properties are degraded; when the diameter is too large, flexibility is degraded. In general, it is preferable that the high-frequency coaxial cable have a diameter of about 10 mm.

The invention is an explosive/illicit drug detection device, described above which is used for body checking, shoe inspection, or mine detection.

Since the detection device is made compact, the detection device can be readily used as a transportable detection device, and is, therefore, suitable for body checking, shoe inspection, and mine detection. In the case where the detection device is used for these applications, no electromagnetic shield is required. Moreover, the existence of explosives and illicit drugs can be reliably confirmed by merely opposing the small and light antenna coil in which noise is considerably reduced to inspection objects at the time of the body checking and shoe inspection, and by merely moving the antenna coil appropriately so that it is opposed to the ground at the time of mine detection.

The invention is further an antenna coil used in the explosive/illicit drug detection device described above,
which is formed in the form of a FIG. 8 with a high-frequency coaxial cable such that two solenoidal coil portions are provided with the coil portions wound in mutually opposite directions and is constituted to use so that it is opposed to an inspection object.

The antenna coil is an invention of an antenna coil suitably used in the explosive/illicit drug detection device of the present invention. It brings about the effects described above.

The invention is also drawn to an explosive/illicit drug detection method comprising:
a opposition step in which the antenna coil discussed above is opposed to an inspection object;
a irradiation step in which the antenna coil irradiates the inspection object with a high-frequency pulse generated by a mean for generating high-frequency pulses as a radio wave;
a reception step in which the antenna coil receives a nuclear quadrupole signal sent out of the inspection object excited by the irradiation of radio wave; and
a detection step in which the antenna coil detects an explosive and/or an illicit drug in the inspection objects based on the nuclear quadrupole signal received by the antenna coil.

The explosive/illicit drug detection method is a method conducted by using the explosive/illicit drug detection device described above. In this invention, by using the small and light antenna coil formed in the form of the FIG. 8 such that the two solenoidal coil portions are provided with the coil portions wound in mutually opposite directions, explosives and illicit drugs can be detected simply and reliably.

Effects of the Invention

The present invention can provide a detection device that is compact and is capable of reliably detecting various explosives and illicit drugs and a detection method using the detection device.

MODE FOR CARRYING OUT THE INVENTION

An embodiment of the present invention will be described below. However, the present invention is not limited to the embodiment described below. Note that various modifications can be made to the embodiment below within a same scope as and a scope equivalent to the scope of the invention.

1. A Configuration of an Explosive/Illicit Drug Detection Device according to an Embodiment of the Present Invention At first, a basic configuration of an explosive/illicit drug detection device according to an embodiment of the invention will be now described.

(1) Basic Configuration of Antenna Unit

Figure 1:
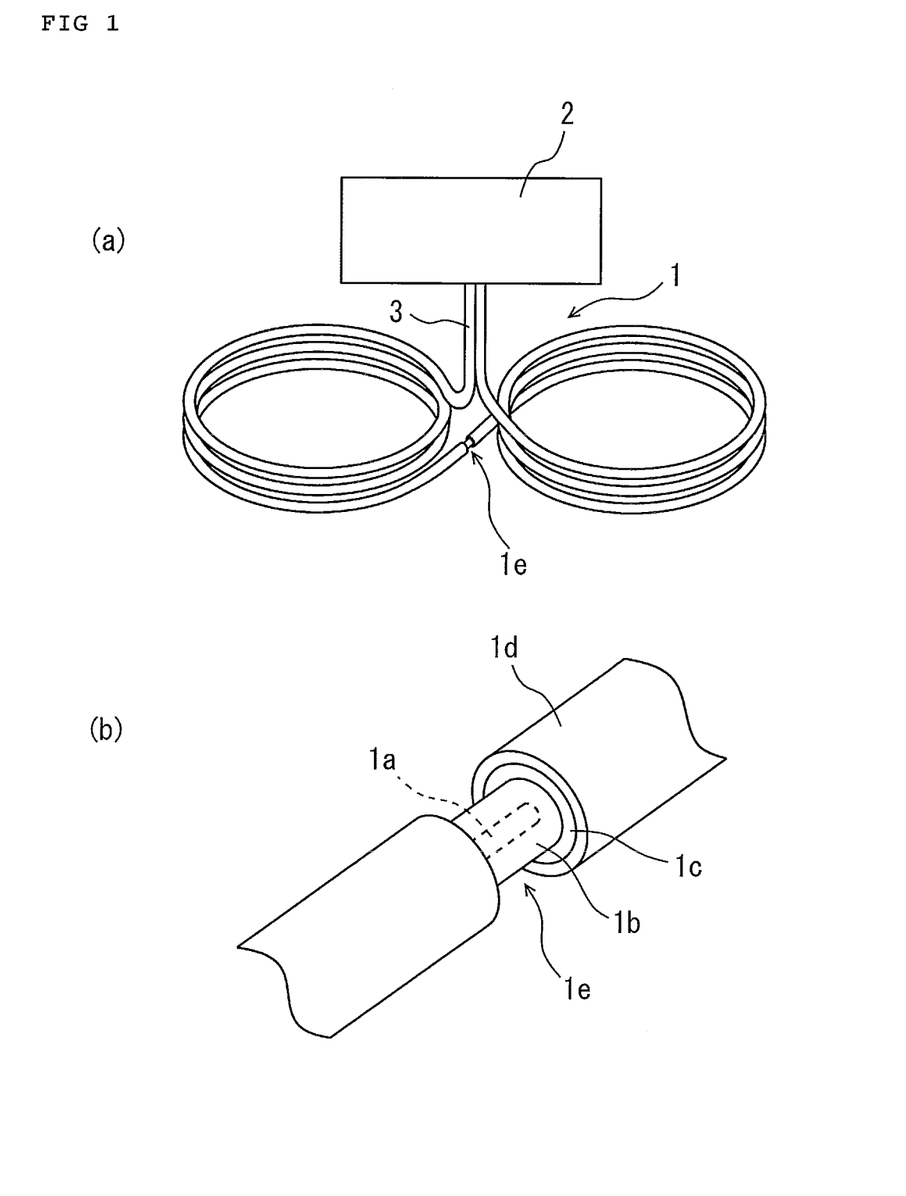
FIG. 1 is an illustration schematically showing a basic configuration of an antenna unit comprised in an explosive/illicit drug detection device according to an embodiment of the present invention.

First, a basic configuration of an antenna unit of the explosive/illicit drug detection device will be described below with reference to FIG. 1. FIG. 1 is a schematic illustration showing the basic configuration of the antenna unit of the explosive/illicit drug detection device according to an embodiment of the invention.

FIG. 1(a) shows a shape of an antenna coil, and FIG. 1(b) shows an enlarged view of the central part of the antenna coil. In FIG. 1(a), reference numeral 1 denotes the antenna coil made of one high-frequency coaxial cable. The antenna coil 1 is constituted by two, i.e., left and right solenoidal coils, and ends of the solenoidal coils are connected to a matching box (MB) 2 through a connection part 3.

In FIG. 1(b), reference numeral 1a denotes a conductor wire having excellent electrical conductivity such as a copper wire, reference numeral 1b denotes an insulator made of PET or the like, reference numeral 1c denotes an electromagnetic shielding material having electrical conductivity, and reference numeral 1d denotes a sheath protective covering. As shown in FIG. 1(b), at one portion of the central part of the antenna coil 1, the electromagnetic shielding material 1c and the sheath protective covering 1d are not provided, and a recessed portion 1e where the inner insulator 1b is exposed is provided. The provision of the recessed portion 1e makes magnetic flux pass through the antenna coil 1 readily.

Since the antenna coil 1 is made of the high-frequency coaxial cable, a reduction in electric field noise can be achieved. Since the two, i.e., the left and right solenoidal coils are opposite in direction of winding to each other, magnetic field noises from distant places can be cancelled. Because of this, unlike conventional antenna units, it is not needed to provide an electromagnetic shield in addition to the antenna coil.

By making antenna coil 1 more compact and reducing the noise as described above, the antenna coil 1 can be directly opposed to an inspection object, there is no need to place an inspection object within the antenna coil 1 unlike conventional antenna coils, and thus the inspection object can be inspected simply and easily.

(2) Basic Principle of Transmission and Reception at Antenna Unit

Figure 2:
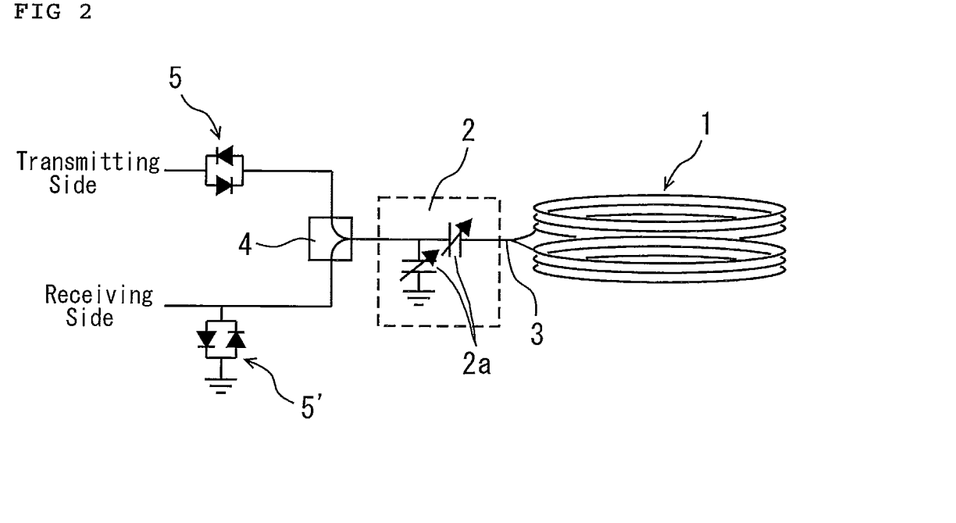
FIG. 2 is a block diagram showing a basic principle of the antenna unit of the explosive/illicit drug detection device according to an embodiment of the invention.

A basic principle of transmission and reception at the antenna unit will be described below with reference to FIG. 2. FIG. 2 is a block diagram showing a basic principle of the antenna unit. In FIG. 2, reference numerals 1, 2, and 3 denote same components as the components 1, 2, and 3 of FIG. 1, reference numeral 4 denotes a power divider, and reference numerals 5 and 5' each denote a cross diode.

A high-frequency pulse generated by a mean for generating high-frequency pulses (not shown) is transmitted and sent to the antenna coil 1 from the transmitting side through the cross diode 5, the power divider 4, and the matching box 2, and then an inspection object is irradiated with a radio wave from the antenna coil 1. A NQR signal, sent out of an explosive or an illicit drug excited by the irradiation of radio wave, is received by the antenna coil 1.

Then, the received NQR signal is sent to a receiving side in the direction opposite to the direction of the transmission, i.e., through the matching box 2, the power divider 4, and the cross diode 5. The matching box 2 is provided with a variable capacitor 2a to make impedance matching at a NQR frequency.

2. Inspection Using the Explosive/Illicit Drug Detection Device according to an Embodiment of the Invention Results of a specific inspection conducted using the explosive/illicit drug detection device according to an embodiment of the invention will be described below with reference to FIG. 3.

Detection of RDX (cyclotrimethylene trinitramine) and TNT (trinitrotoluene) that are kinds of explosive was conducted using a detection device provided with the antenna coil of FIG. 1. An antenna coil was used in which its diameter (inner diameter) is 22 cm, its winding number is 3, and the connecting part 3 has a length of 10 cm.

Figure 3:
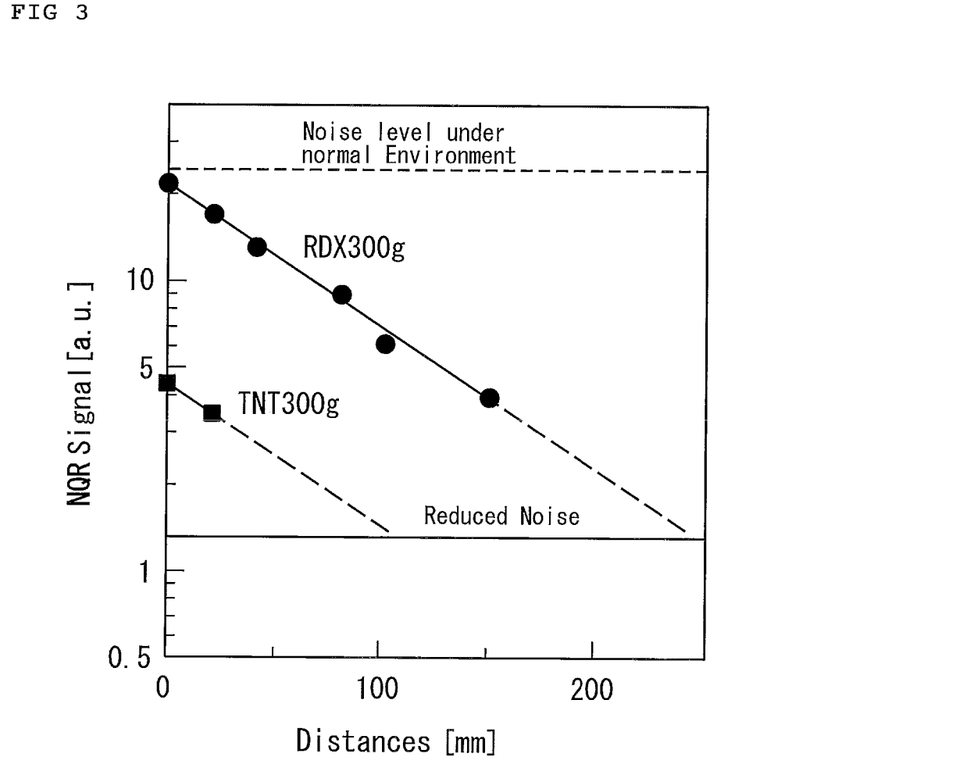
FIG. 3 is a graph showing relations between levels of NQR signals sent out of RDX and TNT and the distances.

The amounts of the RDX and the TNT as detection objects were 300 g. The accumulation time was set at 10 minutes. Then, relations between distances from the antenna coil to the detection objects and Levels of NQR signals were measured. Results of the measurements are shown in FIG. 3. In FIG. 3, black dots each denote a level of the NQR signal of the RDX, and black squares each denote a level of the NQR signal of the TNT.

As shown in FIG. 3, a noise level under a normal environment is 25 a.u., which exceeds the levels of the NQR signals sent out of the RDX and the TNT, and thus it is difficult to detect the NQR signals even in close proximity. In the detection device according to the embodiment, however, since the noise level can be reduced to 1.3 a.u., the NQR signal sent out of the RDX can be detected even when the antenna unit is placed at a distance of 200 mm or longer from the RDX, and the NQR signal sent out of the TNT can be detected even when the antenna unit is placed at a distance of 100 mm or longer from the TNT.

3. A Concrete Example of Use of the Explosive/Illicit Drug Detection Device according to the Embodiment of the Invention A concrete example of use of the explosive/illicit drug detection device according to the embodiment of the invention will be described in more concretely below.

(1) Hand Luggage Inspection Device

The following example is an example of use of the antenna coil of FIG. 1 in a detection device to detect explosives or illicit drugs hidden in hand luggage, freight, and so on.

Figure 4:
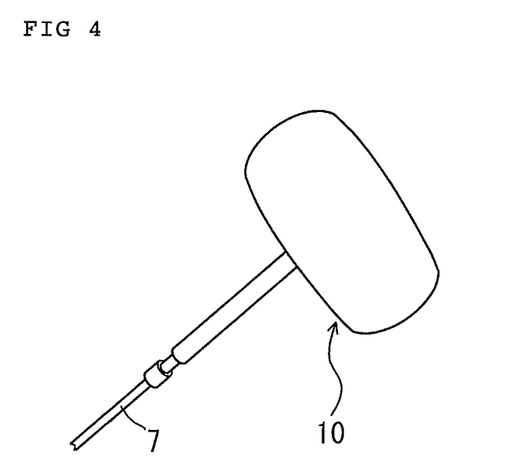
FIG. 4 is an illustration showing an external appearance of an antenna unit comprised in a hand luggage inspection device according to an embodiment of the invention.

FIG. 4 is an illustration showing an external appearance of an antenna unit 10 comprised in the detection device. In FIG. 4, the entire antenna unit 10 is covered with a cover. Within the cover, the antenna coil and the matching box of FIG. 1 are provided. The antenna unit 10 is connected to the main body (not shown) of the detection device through a cable 7.

In accordance with the embodiment, by merely making the antenna unit 10 contact luggage, freight, or the like without passing the luggage, freight, or the like through the detection device, the inspection can be conducted speedily provided that the inspection object is in a substance other than metallic substances. And further, since the antenna unit 10 is compact and light, the detection device is easy to handle and can be carried readily, whereby inspection can be conducted at any desired place.

(2) Body Checker

The following example is an example of use of the detection device according to the embodiment at a body checker to detect explosives or illicit drugs hidden in persons' clothing or persons' bodies.

Figure 5:
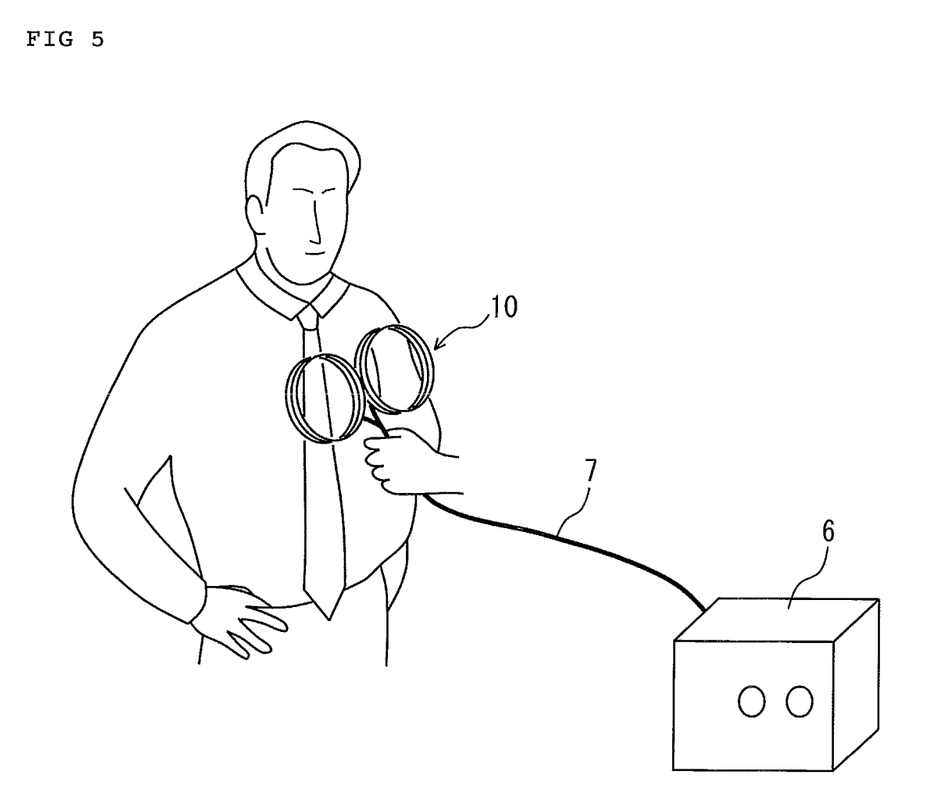
FIG. 5 is an illustration schematically illustrating a state in which inspection is conducted by using a body checker according to an embodiment of the invention.

FIG. 5 is a schematic illustration showing a state in which a check of a person is conducted by using the body checker. Since the antenna unit 10 is downsized and lightened into a hand-held antenna unit, the check can be conducted speedily by merely holding the antenna unit 10 to the person's clothing. Incidentally, in this example as well, the antenna unit 10 with the cover of FIG. 4 is used, but an illustration of the cover covering the antenna unit 10 is omitted in FIG. 5 so that the shape of the antenna coil as a point of the present invention can be imagined readily. In addition, reference numeral 6 denotes a body checker main body, and reference numeral 7 denotes a cable used to connect the antenna unit 10 and the body checker main body 6.

(3) Shoe Inspection Device

The following example is an example of use of the detection device according to the embodiment at a shoe inspection device to detect explosives or illicit drugs hidden in shoes.

Figure 6:
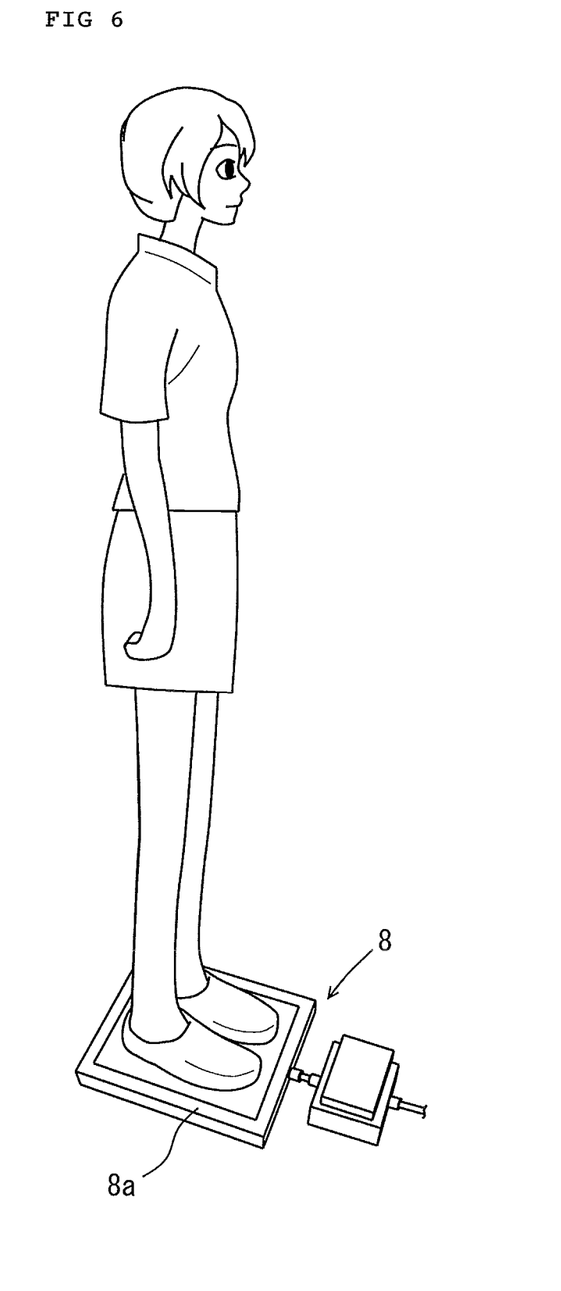
FIG. 6 is an illustration showing an external appearance of an antenna unit and an inspection pad comprised in a shoe inspection device according to an embodiment of the invention.

FIG. 6 is an illustration of an antenna unit 8 and an inspection pad 8a comprised in the shoe inspection device used in this example. Within the inspection pad 8a, the antenna coil is placed so that the coil is opposed to the top surface of the inspection pad 8a.

In accordance with the embodiment, the inspection can be conducted simply and easily by merely getting on the inspection pad 8a with shoes on.

(4) Mine Detection Device

The following example is an example of use of the detection device according to the embodiment at a mine detection device to detect mines buried in the ground.

Figure 7:
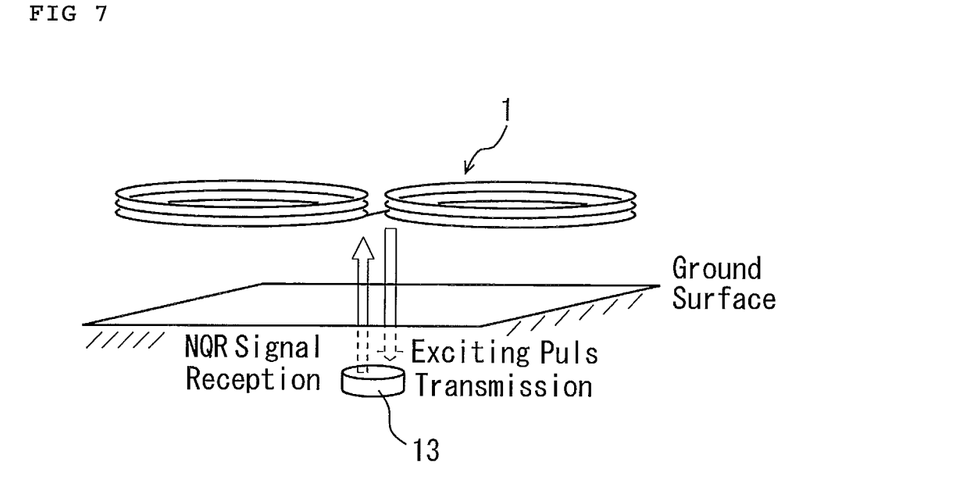
FIG. 7 is an illustration schematically illustrating a state in which a mine is detected by using a mine detection device according to an embodiment of the invention.
Figure 8:
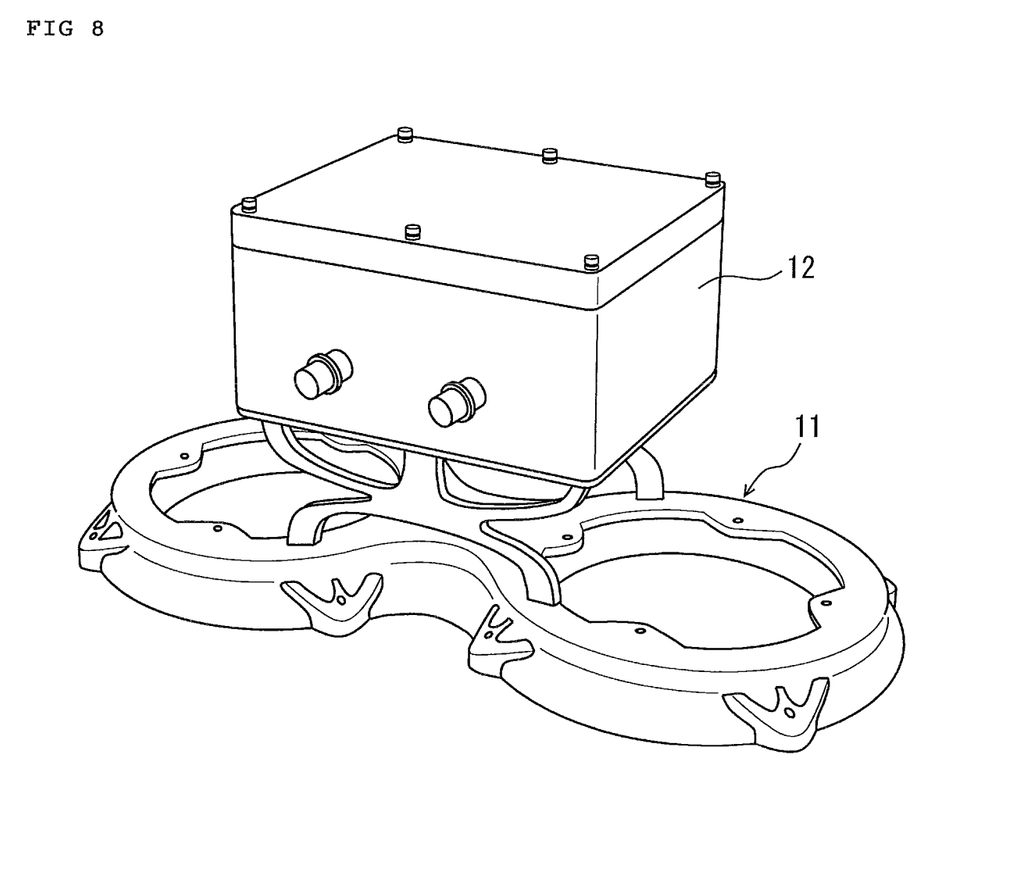
FIG. 8 is an illustration showing an external appearance of a mine detection device according to an embodiment of the invention.

FIG. 7 is an illustration schematically illustrating a state in which mine detection is conducted in this example. And further, FIG. 8 is an illustration showing an external appearance of the antenna coil of the mine detection device and a matching circuit-preamplifier housing box that are used in this example. In this example, as shown in FIG. 7, a mine buried in the ground can be detected from surface of the ground. That is, the mine detection device is moved on the ground surface while emitting radio waves from the antenna coil 1 to the ground. When the antenna coil 1 has been moved above the mine buried in the ground, the antenna coil 1 receives a NQR signal sent out of the explosive in the mine 13 excited by the radio wave, whereby the mine 13 can be detected.

According to the embodiment, the mine detection device of FIG. 8, which is constituted by the antenna coil 11 (with a cover) and the matching circuit-preamplifier housing box 12, is compact and light so that it weighs only about 5 kg. Therefore, it is easy to mount the mine detection device on a robot arm. As a result, mines can be detected by remote control without getting near to mine detection areas, and thus the detection can be conducted safely.

DESCRIPTION OF THE REFERENCE NUMERALS 1, 11, 21 antenna coil
1a conductor wire
1b insulator
1c electromagnetic shielding material
1d sheath protective covering
1e recessed portion
2 matching box
2a variable capacitor
3 connection part
4 power divider
5, 5' cross diode
6 body checker main body
7 cable
8, 10 antenna unit
8a inspection pad
12 matching circuit-preamplifier housing box
13 mine
22, 23 electromagnetic shield
24 personal computer
25 bag
26 inspection object

The invention claimed is:

1. An explosive/illicit drug detection device comprising
a mean for generating a high-frequency pulse;
an antenna coil that irradiates an inspection object with the generated high-frequency pulse, input through matching means having a cross diode and a variable capacitor, as a radio wave and receives a nuclear quadrupole signal sent out of the inspection object excited by the radio wave; and
a detection mean for detecting an explosive and/or an illicit drug hidden in the inspection object based on the received nuclear quadrupole signal,
wherein the antenna coil is formed by winding a high-frequency coaxial cable in the form of a FIG. 8 so that two solenoidal coil portions are provided on the same plane with the coil portions wound more than once in mutually opposite directions, a recessed portion being provided at the high-frequency coaxial cable connecting the two solenoidal coil portions, and
is used so that it is opposed to inspection objects.

2. The explosive/illicit drug detection device according to claim 1 which is used for body checking, shoe inspection, or mine detection.

3. An antenna coil used in the explosive/illicit drug detection device according claim 1 or 2, which is formed in the form of a FIG. 8 with a high-frequency coaxial cable such that two solenoidal coil portions are provided on the same plane with the coil portions wound more than once in mutually opposite directions and is constituted to use so that it is opposed to an inspection object, and wherein a recessed portion is provided at the high-frequency coaxial cable connecting the two solenoidal coil portions.

4. An explosive/illicit drug detection method comprising:

a opposition step in which the antenna coil according to the claim 3 is opposed to an inspection object;

a irradiation step in which the antenna coil irradiates the inspection object with a high-frequency pulse generated by a mean for generating high-frequency pulses as a radio wave;

a reception step in which the antenna coil receives a nuclear quadrupole signal sent out of the inspection object excited by the irradiation of radio wave; and a detection step in which the antenna coil detects an explosive and/or an illicit drug in the inspection objects based on the nuclear quadrupole signal received by the antenna coil.

\* \* \* \* \*